(12) United States Patent
Orten

(10) Patent No.: US 6,485,408 B2
(45) Date of Patent: Nov. 26, 2002

(54) ERECTION AID

(75) Inventor: Birger Orten, Alesund (NO)

(73) Assignee: Meditron AS, Vettre (NO)

( * ) Notice: Subject to any disclaimer, the term of this patent is extended or adjusted under 35 U.S.C. 154(b) by 0 days.

(21) Appl. No.: 09/775,247

(22) Filed: Feb. 1, 2001

(65) Prior Publication Data

US 2002/0022760 A1 Feb. 21, 2002

(30) Foreign Application Priority Data

Mar. 14, 2000 (NO) ................................................. 001333

(51) Int. Cl.⁷ ................................. A61F 5/00; A61F 6/04
(52) U.S. Cl. ............................................. 600/38; 128/844
(58) Field of Search ......................... 600/38–45, 324, 600/454, 551; 604/20; 601/15; 128/844

(56) References Cited

U.S. PATENT DOCUMENTS

| | | | | |
|---|---|---|---|---|
| 4,881,526 A | * | 11/1989 | Johnson et al. ............... | 601/15 |
| 4,909,263 A | * | 3/1990 | Norris ........................ | 600/551 |
| 5,163,447 A | * | 11/1992 | Lyons ........................ | 128/844 |
| 5,377,692 A | * | 1/1995 | Pfeil ......................... | 128/844 |
| 5,524,638 A | * | 6/1996 | Lyons ........................ | 128/844 |
| 6,169,914 B1 | * | 1/2001 | Hovland et al. ............. | 600/324 |
| 6,251,076 B1 | * | 6/2001 | Hovland et al. ............. | 600/454 |
| 6,266,560 B1 | * | 7/2001 | Zhang et al. ................ | 604/20 |

FOREIGN PATENT DOCUMENTS

| | | | | |
|---|---|---|---|---|
| WO | 92/09962 | * | 6/1992 | ........... G06F/15/42 |
| WO | 01/70150 A1 | * | 9/2001 | ............. A61F/5/41 |

* cited by examiner

Primary Examiner—Kevin Shaver
Assistant Examiner—Nikita R Veniaminov
(74) Attorney, Agent, or Firm—Ladas & Parry

(57) ABSTRACT

An erection aid comprises an elastic device adapted to be placed around at least a part of a penis, which device is in the form of a condom (1) or a tightening ring (10). The device is equipped with a piezoelectric unit (3), for example a piezoelectric foil, for emission of stimulating vibrations. The device is self-supplied with a battery (7) and an electronic miniature circuit (4) for activation of the piezo-unit (3).

14 Claims, 3 Drawing Sheets

ERECTION AID

BACKGROUND OF THE INVENTION

1. Field of the Invention

The present invention relates to a mechanical/electromechanical erection aid. At the outset this means an aid to remedy a dysfunction, viz. lack of erection or an erection that declines too rapidly, but also an aid to provide an additional stimulus in connection with a normal erection situation.

2. Background Art

Various remedies of chemical and mechanical type are previously known in connection with erectile dysfunction. Chemical agents can be administered by injection into or near penis, or they can be taken orally, compare the medicament "Viagra". However, chemical remedies are burdened with adverse effects, and injections will feel unpleasant for many persons. Among the commonly known mechanical erection aids are vacuum pumps for obtaining erection, and tightening devices e.g. round the root of the penis for maintaining an obtained erection.

A device of the last mentioned type Is previously known from German "Offenlegungsschrift" Patent DE 22 07 169, but this device is equipped, in addition to the proper tightening device intended to prevent the reverse flow of blood from the penis, with further devices intended to stimulate the sexual partner, inter alia an electrical vibrator device. Hence, this vibrator device is only intended for the partner, and is arranged as a separate unit at a distance from the penis. The vibrator device itself is not specified further, and is powered from a battery situated somewhere else.

An annular amusement device and a condom-shaped amusement device are known from U.S. Pat. No. 5,524,638 and U.S. Pat. No. 5,163,447 respectively, both amusement devices producing mechanical vibrations in the form of sound, more particularly music. In both cases, the body contact between two sexual partners will trigger music playback from a unit which, also in this case, is situated close to the root of the penis, but outward from the penis. The unit may contain a vibration element, i.e., a sound emitter, which may be, e.g., a piezoelectric miniature loudspeaker, further an electronic microchip, and a small battery for powering the loudspeaker and the microchip. However, these amusement devices are not manufactured, and not suitable, to remedy an erectile dysfunction.

Further, a so-called "vibrating condom" is known from U.S. Pat. No. 5,377,692, which condom is intended to stimulate the genitals of the sexual partner during coitus. One embodiment of this condom utilizes an embedded sheet of "Nitinol", together with a battery. The Nitinol sheet has shape memory, and can be flexed by means of electricity. Using a pulsed current, the sheet is able to provide mechanical vibrations for stimulation of the genitals of the sexual partner. It does not appear from this patent what triggers the vibration function.

Not even this last mentioned US-patent aims at remedying or relieving the male lacking or diminishing erection dysfunction, it is actually stated explicitly in the patent that this is not the intention.

Thus, there is still a lack of an effective mechanical aid for the erection dysfunction that is not perceived as being a nuisance, or that is not difficult to use.

The present invention aims at meeting this lack, and intends to provide an erection aid that is easy to slip on and that is perceived as comfortable also for the sexual partner.

This aim is obtained by providing an erection aid such as defined in the appended independent patent claim 1. Preferred embodiments of the invention appear from the dependent claims 2–10. In the following, the invention shall be illuminated further by discussing exemplary embodiments, and it is at the same time referred to the appended drawings, in which

BRIEF DESCRIPTION OF THE DRAWINGS

Figure 1:
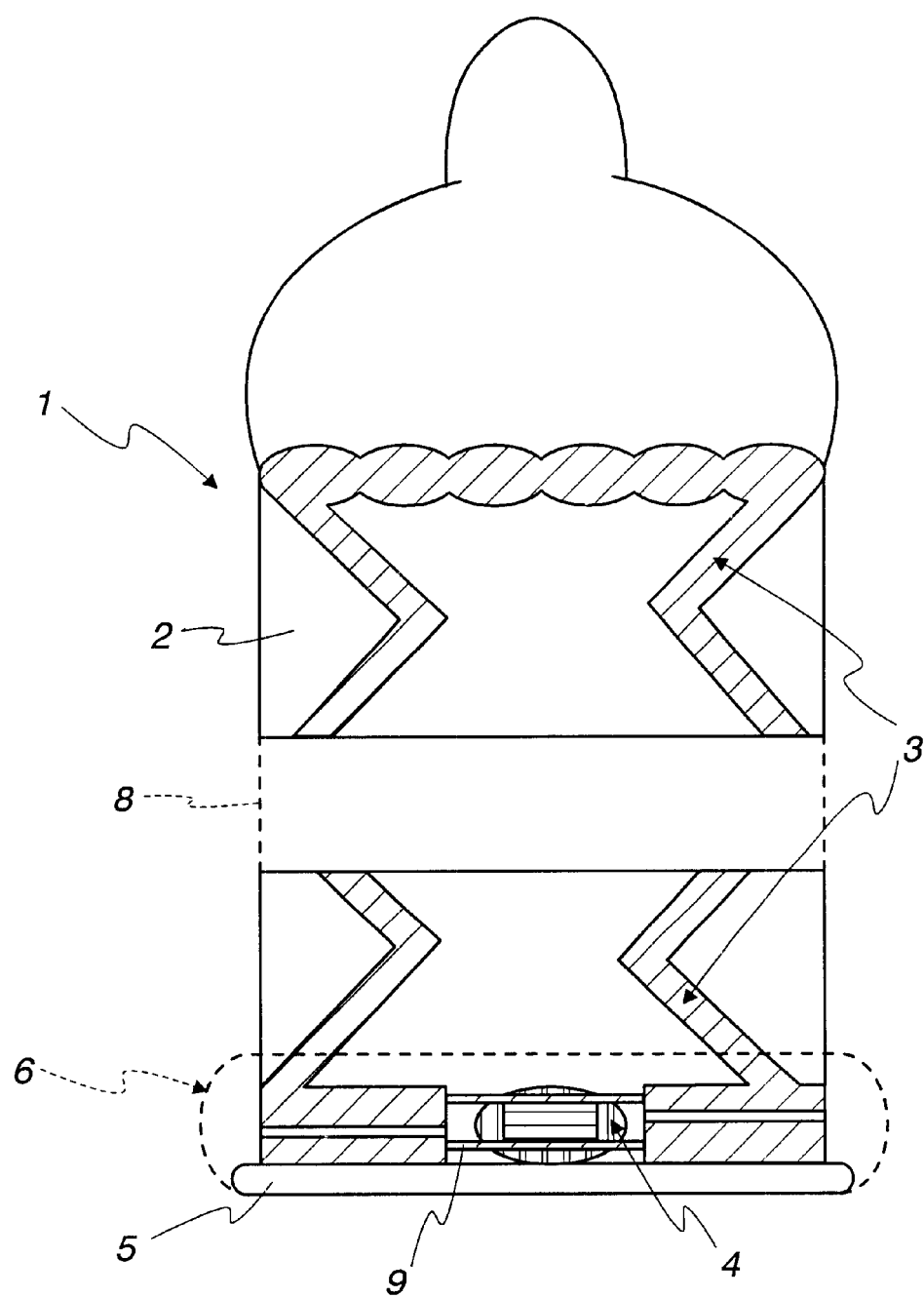
FIG. 1 shows an embodiment of the invention in the form of a condom.

FIG. 1 depicts, in a schematic manner, a condom 1 which constitutes a first embodiment of the invention. The condom 1 appears broken at a midsection 8 along its length, from drawing reasons. The condom 1 is made from an ordinary material 2, i.e. from a suitable rubber type, e.g. latex rubber.

In the shown embodiment, the condom 1 is equipped with an electronic miniature circuit 4 near the condom opening. The condom 1 has an ordinary collar 5 at the opening. The collar 5 may have a tightening function. Thin electrical conductors 9 extend from the circuit 4 to areas having a piezoelectric foil 3 embedded in the rubber 2, for instance with equal thicknesses of rubber outside on both sides. The proximal foil parts 3 extend in a circumferential direction, but further on from these parts there are foil strips 3 extending mainly in a direction along the condom 1. These foil strips are shown in a zigzag arrangement, but may equally well extend in straight line fashion, in a spiral shape or in some other manner. However, it is an advantage of the zigzag shape that the foil 3 then easily can take part in a change of shape of the condom. A piezoelectric section is also shown near the penis head part, with a view to special boost in this area.

The thin conductors 9 can be substituted by thin sections of the piezoelectric material itself.

Polyvinyl fluoride is utilized as the preferred piezoelectric foil material, however other types of foil to be found on the market, can also be used.

An alternative embodiment 6 is shown by means of a dotted line, wherein the opening collar 5 of the condom has been made wider in order to accommodate the electronic circuit 4 and battery 7. The battery 7 does not appear in this drawing, but may for instance be situated on the diametrically opposite side, like in the embodiment appearing in FIG. 2, or the battery 7 and the circuit 4 may be arranged close to each other on the circumference, or even together.

The miniature circuit 4 may be a so-called hybrid circuit, an ASIC circuit or it may consist of separate components, possibly arranged on a small circuit board. This circuit board may also be of a soft type.

The miniature circuit 4 can be provided with a special switch arranged to trigger activation when a condom sales package is opened, and the circuit will then be activated continuously until the battery is empty. Or possibly there may be arranged a special switch for manual start of circuit activity, e.g. a touch sensitive switch.

The miniature circuit delivers voltage pulses, or for instance sinusoidal oscillations, to the piezoelectric foil 3, which foil thereby goes into a state with mechanical vibrations which are felt in penis areas, and additionally, even the electrical potentials can be sense. In this manner, penis can be stimulated to a prolonged erection and increased erection. (When the condom embodiment is used, it is presupposed that a preliminary erection has been obtained, because if not, the practical application of a condom is not a simple matter.)

The miniature circuit 4 is arranged to oscillate with a certain frequency, or with several superposed frequencies. Possibly, several separate circuits can be used, each oscillating with its respective frequency. The frequencies involved may be low "massage" frequencies in a low frequency audio range or a sub-audio range, or high frequencies (ultrasound frequency range) may be used.

With a certain type of miniature battery, e.g. a flat battery with limited capacity, one may also insert several such batteries, for instance in an extended collar 6. Purpose-built batteries can also be used, particularly with regard to shape. A larger battery may also work as a "backing mass" for a foil, i.e. a battery mass of for instance 10 g will, relative to a foil mass of for instance 0,1 g, act as a backing mass so that the vibration is concentrated in the foil. (One may also include a special weight member for this purpose.)

The piezoelectric foil 3 can be arranged quite close to the inside of the condom 1, i.e. only covered by a super-thin rubber layer, in order that the vibrations shall be felt more strongly. The opposite opportunity is also possible, and one may even prepare embodiments in which the piezoelectric foil is put on the outside, for lowered sensitivity, and fully on the inside, for maximum effect. What is perceived as pleasant or unpleasant may vary from person to person.

Another variant to be encompassed by the invention, is an embodiment in which there is used two layers of foil with rubber therebetween, and with outer super-thin rubber layers.

The piezoelectric foil 3 may also cover much larger, connected areas of the penis than what is shown in FIG. 1, i.e. with a foil having a shape more like a sheet, or preferably as a wicker work or trellis. A wicker shape will follow elastic shape changes more easily.

A piezoelectric foil can be made very thin, for instance a thickness of 28 μm is a standard product.

The invention comprises also the embodiment in which the piezoelectric material does not appear in a foil shape, but is thicker, compare bimorph or ceramic elements shaped as strips, rectangles or thin circular disks, with electric conductors thereto from circuit 4. For the condom embodiment this will then first and foremost apply to an extended collar 6 which can accommodate such other types of piezoelectric material, like polyvinyl fluoride, bimorph or ceramic elements. Possibly, several layers of foil can be used. Other electromechanical or piezo-type function than piezoelectricity can also be used, for instance shape memory effect with rapid motion, piezo-magnetism, electrically driven thermophone effect etc. Possibly, special condoms, for example equipped with ribs, may is also accommodate such variants.

Furthermore, the condom variant is also intended to comprise a quasicondom with a forward opening, that is for the case in which transfer of semen or conception is desirable. Such a quasi-condom is also a useful solution in the previously mentioned case with a problematic preliminary erection, since such a quasi-condom can be applied to a non-erect limb without experiencing problems after obtaining an erection.

In the case without an enlarged collar, it is important that especially the battery 7 and the electronic circuit 4 do not feel uncomfortable for any one of the partners, and therefore, it is particularly important with flat designs of these units, while also maintaining small dimensions laterally. With an extended collar 6, the shape of these units are somewhat less important.

An added effect to be achieved in addition to the main effect that regards erectile dysfunction, is of course an effect of increased stimulation for the penis, even for a person having a normal erection, that is without dysfunction. Hence, the erection aid in accordance with the invention, may also be of interest for persons having a normal erection, in fact also for persons in a sexual situation without a partner.

It is also an additional effect that a sexual partner may feel the vibrations emitted, and there should be no problem providing embodiments that will also show special consideration for a partner, by providing for instance piezo-foil 3 in condom areas selected with particular regard to certain anatomic parts of the partner, for example particular positions in and near the vaginal entrance. In particular the embodiment with a foil 3 arranged on the outside, will provide vibrations which are quite noticeable for the partner, but also the inside foil arrangement will provide an effect that will be noticed by the partner.

Figure 2:
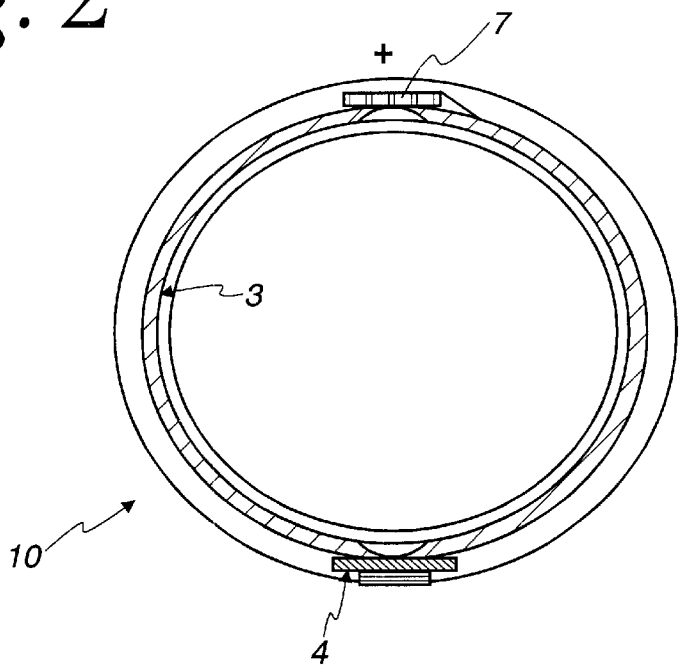
FIGS. 2, 3 and 4 show an embodiment in the form of a tightening ring.
Figure 3:
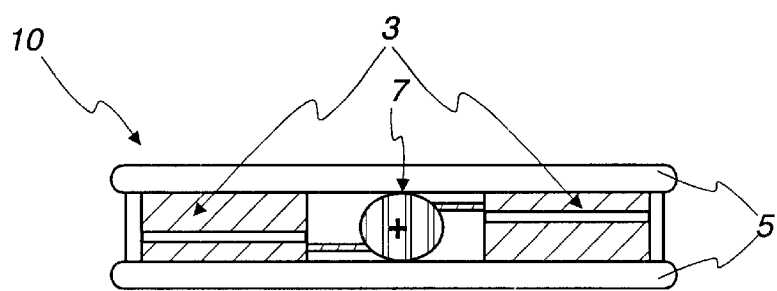
Figure 4:
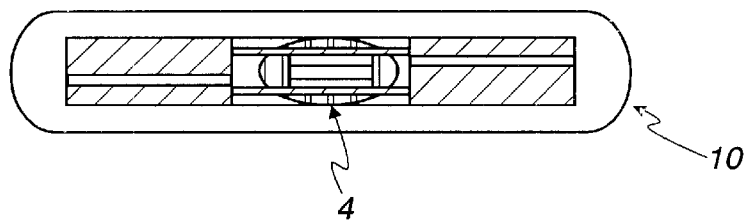

In FIGS. 2, 3 and 4 appears a different embodiment of the erection aid in accordance with the invention. This embodiment is based on a classical tightening ring 10, and is preferably made of rubber, but quite much thicker than condom rubber, that is, more like for instance the previously mentioned "extended collar", or even somewhat thicker.

In this case it is only a matter of producing stimulating pulses in an annular area, preferably at the root of the penis, or around some other area further out on the penis. This variant will be able to deal with the problem of a lacking preliminary erection, and will then possibly also be useful in cooperation with a condom variant, that is, the ring 10 first in order to achieve an erection, and thereafter mounting of the condom 1 to provide further effect (and of course to provide the normal condom function).

For the rest, the ring 10 will work in a corresponding manner as the previously mentioned condom 1, or in particular in the same manner as the mentioned "enlarged collar" 6. Battery/batteries 7, miniature circuit/circuits 4 are accommodated inside the ring 10, piezo-foil 3 may be arranged on the inside thereof, or embedded in the bulk of the rubber. The ring 10 will also accommodate piezoelectric material of another type than the thin foil, such as previously mentioned. The ring can be manufactured in various widths, for instance in the range 0,5–5 cm.

FIGS. 3 and 4 show two external designs of the tightening ring 10, one design with two edge collars 5 and thinner rubber therebetween in FIG. 3, and one design in FIG. 4 with a smooth rounding. It appears also that the battery 7 and the circuit 4 are provided at diametrically opposite sides, but this is no necessity. With regard to the embodiment of FIG. 3, it is also possible to remove one of the collars, to provide a variant towards the previously mentioned "quasicondom".

Figure 5:
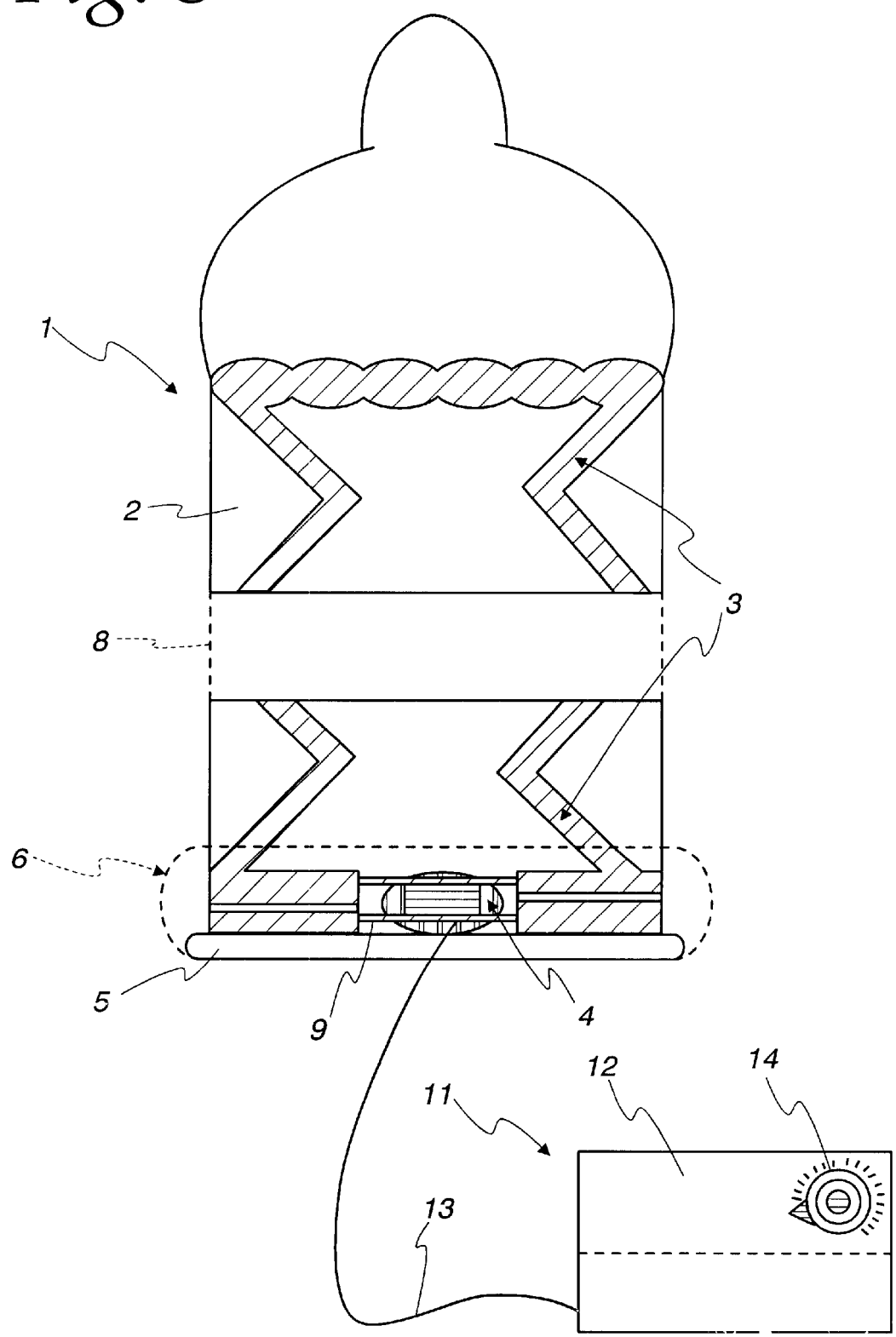
FIG. 5 shows an embodiment that corresponds to the embodiment of FIG. 1, but with an extra feature in the form of an external power supply unit.

In FIG. 5 the same sort of condom device 1 as in FIG. 1 is depicted, however with an extra feature in the form of an external power supply unit 11 that is connected to the miniature circuit 4 via a cable 13. The point of using such an external unit 11, is at first to provide stronger power signals to the piezo-elements 3 than what can be obtained using only built-in batteries in the erection aid itself.

But in a more advanced embodiment, the power supply unit 11 is also equipped with a control section 12, i.e. a built-in circuit device having manual operator controls 14 and being adapted for signal cooperation with the miniature circuit 4. The user may then for example adjust parameters regarding the signal emission from the aid, for instance power, signal frequency, duration, pulse shape etc. For illustrative purposes only one operator control 14 is shown on the control section 12 of the power supply unit.

Such an embodiment with an external power supply unit is of course also valid in connection with the variants shown in FIGS. 2, 3 and 4.

The cable 13 may contain several separate conductors for power currents to the piezo-elements and for control signals between the miniature circuit 4 and the control section 12. At the end of cable 13 a flat special connector is provided that cooperates with a corresponding special connector on the miniature circuit 4.

I claim:

1. An erection aid adapted to be placed around a part of a penis, comprising:
    a device of elastic material equipped with a piezo-material connected to an electronic miniature circuit that delivers voltage pulses or sinusoidal oscillation to said piezo-material; and
    a miniature battery,
        wherein said miniature battery and said miniature circuit are arranged in or on the device, and
        wherein the piezo-material is adapted to give off mechanical pulses or vibration to said penis or parts thereof upon activation of the miniature circuit.

2. The erection aid of claim 1, wherein the piezo-material is a piezoelectric material.

3. The erection aid of claim 2, wherein the piezo-material is designed to give off mechanical and electrical pulses or vibration to a sexual partner during coitus.

4. The erection aid of claim 2, wherein said piezoelectric material is embedded in the device to avoid direct skin contact.

5. The erection aid of claim 2, wherein said piezoelectric material is a strip or a trellis shaped to follow the elasticity of the device.

6. The erection aid of claim 1, wherein the miniature circuit is adapted to emit electric pulses or vibration in one or more predetermined frequency ranges.

7. The erection aid of claim 1, wherein the device is adapted to provide an additional function of elastic tightening around the penis.

8. The erection aid of claim 1,
    wherein the device is constituted by a condom;
    wherein the miniature circuit and the miniature battery are placed in a collar at an edge by the open end of said condom; and
    wherein one or more piezo-materials are arranged in a condom area that corresponds to a particularly favorable penis area with regard to nerve stimulation.

9. The erection aid of claim 1, wherein the device is constituted by an elastic tightening ring adapted to be slipped onto the penis.

10. The erection aid of claim 1, wherein the miniature circuit is adapted to be activated automatically upon opening of a sales package or manually when the device is slipped onto the penis.

11. The erection aid of claim 1, wherein the piezo-material is adapted to give off electrical pulses or vibration to a part of the penis upon activation of the miniature circuit.

12. An erection aid adapted to be placed around a part of a penis, comprising:
    a device of elastic material equipped with a piezo-material connected to an electronic miniature circuit that delivers voltage pulses or sinusoidal oscillation to said piezo-material; and
    a miniature battery,
        wherein said miniature battery and said miniature circuit are arranged in or on the device, and
        wherein the piezo-material is a piezoelectric foil and is adapted to give off mechanical pulses or vibration to said penis or parts thereof upon activation of the miniature circuit.

13. An erection aid adapted to be placed around a part of a penis, comprising:
    a device of elastic material equipped with a piezo-material connected to an electronic miniature circuit that delivers voltage pulses or sinusoidal oscillation to said piezo-material; and
    a miniature battery,
        wherein said miniature battery and said miniature circuit are arranged in or on the device, and
        wherein the piezo-material is adapted to give off mechanical pulses or vibration to said penis or parts thereof upon activation of the miniature circuit, and the miniature circuit is connectable to an external power supply unit to obtain particularly powerful pulses or vibration.

14. The erection aid of claim 13, wherein said external power supply unit comprises a manually operable signal control device for cooperation with the miniature circuit.

\* \* \* \* \*